(12) United States Patent
Dudley

(10) Patent No.: US 9,993,632 B2
(45) Date of Patent: Jun. 12, 2018

(54) CONNECTION FOR SYRINGE FOR IV BAG INJECTION

(71) Applicant: GAMOLIN LIMITED, Hong Kong (CN)

(72) Inventor: Charles Dudley, Moone (IE)

(73) Assignee: Gamolin Limited, Hong Kong (CN)

( * ) Notice: Subject to any disclaimer, the term of this patent is extended or adjusted under 35 U.S.C. 154(b) by 298 days.

(21) Appl. No.: 14/340,646

(22) Filed: Jul. 25, 2014

(65) Prior Publication Data

US 2015/0265826 A1    Sep. 24, 2015
US 2016/0346527 A9    Dec. 1, 2016

(30) Foreign Application Priority Data

Sep. 19, 2013 (GB) .................................. 1316616.0

(51) Int. Cl.
| | |
|---|---|
| *A61M 39/00* | (2006.01) |
| *A61M 39/02* | (2006.01) |
| *A61B 17/132* | (2006.01) |
| *A61M 5/32* | (2006.01) |
| *A61M 5/34* | (2006.01) |

(Continued)

(52) U.S. Cl.
CPC ..... *A61M 39/0208* (2013.01); *A61B 17/1327* (2013.01); *A61M 5/3202* (2013.01); *A61M 5/3213* (2013.01); *A61M 5/345* (2013.01); *A61M 39/10* (2013.01); *A61M 39/24* (2013.01); *A61M 39/26* (2013.01); *A61M 2039/0205* (2013.01); *A61M 2039/1066* (2013.01)

(58) Field of Classification Search
CPC .............. A61M 5/3202; A61M 5/3212; A61M 5/344–5/348; A61M 39/10; A61M 2039/1066
See application file for complete search history.

(56) References Cited

U.S. PATENT DOCUMENTS 4,232,669 A * 11/1980 Nitshke ................ A61M 5/3202
                                                            604/192
4,607,671 A * 8/1986 Aalto .................... A61J 1/2089
                                                            141/329

(Continued)

FOREIGN PATENT DOCUMENTS

| WO | WO 00/13727 | 3/2000 |
| WO | WO 2003/051430 | 6/2003 |

(Continued)

OTHER PUBLICATIONS

PCT/IB2014/064635 International Search Report and Written Opinion dated Feb. 11, 2015, 10 pages.

*Primary Examiner* — Benjamin Klein
(74) *Attorney, Agent, or Firm* — Dority & Manning, P.A.

(57) ABSTRACT

A connection between a guard tube and a needle holder for a syringe for injecting medication into an IV bag, the guard tube having a needle holder receiving end having an aperture for the needle holder to be inserted from the outside, the aperture terminating at an inner end face, the needle holder having an aperture-penetrating portion having a rim wider than the aperture, or than a step in the aperture, that can be pushed through the aperture to snap fit over the end face or over the step and resist retraction therefrom by a force F which is greater than forces normally experienced by the aperture penetrating portion after it has effected a snap fit.

9 Claims, 3 Drawing Sheets

(51) Int. Cl.
*A61M 39/24* (2006.01)
*A61M 39/26* (2006.01)
*A61M 39/10* (2006.01)

(56) References Cited

U.S. PATENT DOCUMENTS

| | | | |
|---|---|---|---|
| 4,834,716 A | | 5/1989 | Ogle, II |
| 5,607,392 A | * | 3/1997 | Kanner ................. A61M 39/14 128/898 |
| 5,735,823 A | | 4/1998 | Berger |
| 6,070,623 A | * | 6/2000 | Aneas .................... A61J 1/2096 141/27 |
| 6,077,253 A | * | 6/2000 | Cosme ................. A61M 5/3243 128/919 |
| 2006/0155257 A1 | * | 7/2006 | Reynolds ............. A61J 1/2096 604/414 |
| 2007/0078409 A1 | | 4/2007 | Saltz |
| 2016/0158518 A1 | * | 6/2016 | Hallynck ............. A61M 5/347 604/500 |

FOREIGN PATENT DOCUMENTS

| | | | | |
|---|---|---|---|---|
| WO | WO 03051430 A1 | * | 6/2003 | ............ A61J 1/2096 |
| WO | WO 2004/041148 | | 5/2004 | |

\* cited by examiner

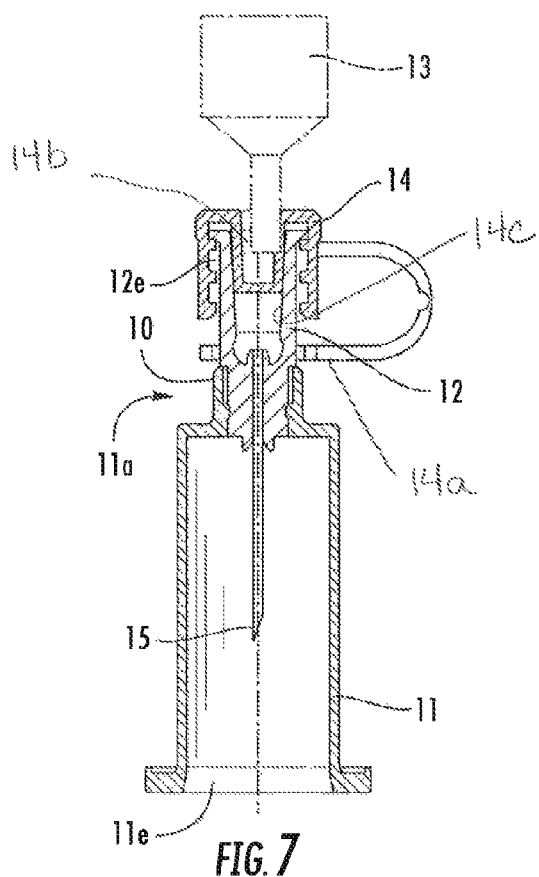
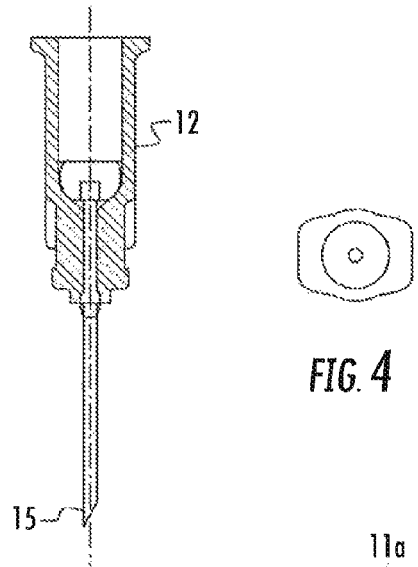
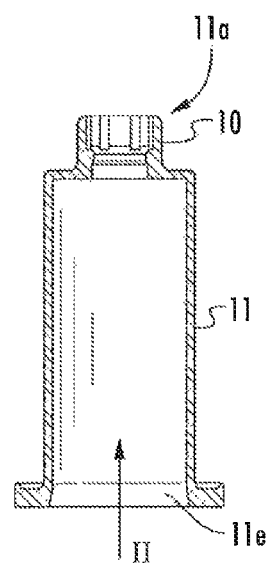
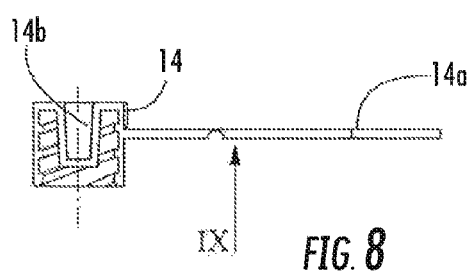
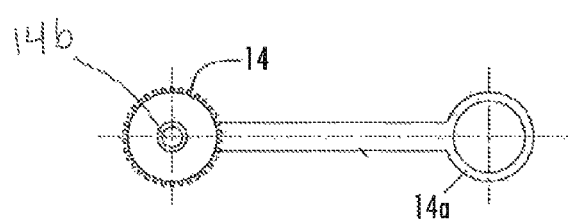
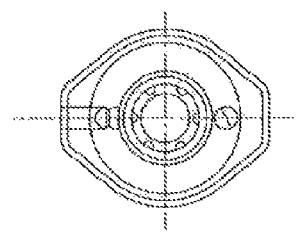

CONNECTION FOR SYRINGE FOR IV BAG INJECTION

FIELD OF THE INVENTION

This invention relates to connections for syringes for IV bag injection.

BACKGROUND OF THE INVENTION

IV bags contain saline and/or glucose solution for continuous intravenous injection. It is often desired to administer other medication, drugs or drug combinations, at the same time, and IV bags are provided for this purpose with a formation including a seal through which such medication can be injected from a syringe through a needle that penetrates the seal, which is capable of self-sealing, possibly numerous times, after the needle is removed.

Needle stick injuries are a problem that has been addressed in many ways, often by using a retraction mechanism that retracts the needle into a shield or sheath after use to inject a patient.

An arrangement involving a guard that essentially permanently encloses the needle was proposed in WO 2000/013727 for the reverse operation, namely drawing medicament into a syringe from a vial prior to injecting the patient. Here, there was concern about risks in changing needles after filling the syringe. The arrangement had an injecting needle surrounded by a sheath used to penetrate the vial seal, both surrounded by a guard attached by a frangible connection, the points of both needles being within the guard so as to be inaccessible to human fingers. Breaking off the guard and sheath gives access to the needle, which can then be used for the injection.

WO03/051430 discloses a needle stick injury prevention arrangement specifically for use with IV bags, in which the needle is enclosed within an open-ended shield, its point some distance inside the open end. This is possible, as the IV bag has a tailed injection arrangement, in which the seal is at the end of a tube, and the point of the needle of the syringe can be concealed well within the shield, yet be able to penetrate the seal while the shield is advanced up the tube. The point is still concealed when the cannula is withdrawn together with the shield.

Problems were encountered with this arrangement, however, particularly in regard to the connection of the needle to the shield. The attachment methods described in WO03/051430 include adhesive or solvent welding, for permanent attachment, or, for fitting at time of use, an interference fit or a click fit. Adhesive or solvent welding have proved problematic in manufacture, while interference, screw and click fit connections have failed in use, with attendant risk of needle stick injury, even enhanced risk on account of the failure mode.

BRIEF DESCRIPTION OF THE INVENTION

The present invention provides an improved connection that is capable of trouble free manufacture and that has no, or substantially reduced, risk of failure during the critical operations of attachment to and removal from the IV bag.

The invention comprises a connection between a guard tube and a needle holder for a syringe for injecting medication into an IV bag, the guard tube having a needle holder receiving end having an aperture for the needle holder to be inserted from the outside, the aperture terminating at an inner end face, the needle holder having an aperture-penetrating portion having a rim wider than the aperture, or a step in the aperture, that can be pushed through the aperture to snap fit over the end face or over the step and resist retraction therefrom by a force F which is greater than forces normally experienced by the aperture penetrating portion after it has effected a snap fit.

Among those forces, of course, may be counted the force that may be exerted when the syringe is removed from the IV bag, which might be effected by pulling on the syringe. A value for F of 30 N has been found adequate to prevent accidental pulling out, but 40 N is preferred.

The entrance to the aperture and/or the penetrating portion should be rounded or chamfered so that pushing the penetrating portion into the aperture either spreads the aperture or compresses the penetrating portion or both using a force which is manageable for manual fitting, and to an extent that the penetrating portion fits inside the aperture, enabling it to pass through. No chamfer or rounding is required for pulling the penetrating portion out of the aperture, as it is not intended that this should be done.

Either the aperture or the penetrating portion or both may be made of resilient plastics material such as polypropylene, ABS or PET.

The aperture and the aperture-fitting portion may have interengaging ribs to prevent relative rotation.

The needle holder may be adapted to fit a syringe with a luer lock fitting or a slip tip fitting, and may be provided with an adapter so that it will accept either syringe fitting. The adapter may be in the form of a flexible tab with a collar that fits over the needle holder and that has a luer lock fitting that fits into a slip tip fitting. The luer lock fitting may be retained in place by screwing over a thread on the end of the adapter.

Dimensioning is important to provide a safe and effective connection. The guard tube must not be so long that the needle cannot reach the IV bag seal, but must also be long enough for the needle tip to be located safely inside it, where a finger cannot reach down. When fitted, the needle tip is desirably no less than 10 mm and no more than 14 mm from the open end of the guard tube.

BRIEF DESCRIPTION OF THE DRAWINGS

A connection according to the invention will now be described with reference to the accompanying drawings, in which:

FIG. 1 is a lengthwise section through a guard tube;
FIG. 2 is a view on Arrow II of FIG. 1;
FIG. 3 is a lengthwise section through a needle holder;
FIG. 4 is an end-on view of the needle holder of FIG. 3:
FIG. 7 is a lengthwise section through the assembled needle holder and guard tube of the previous Figures;
FIG. 8 is a section through a syringe fitting adapter;
FIG. 9 is a view on Arrow IX of FIG. 8.

DETAILED DESCRIPTION OF THE INVENTION

Figure 5:
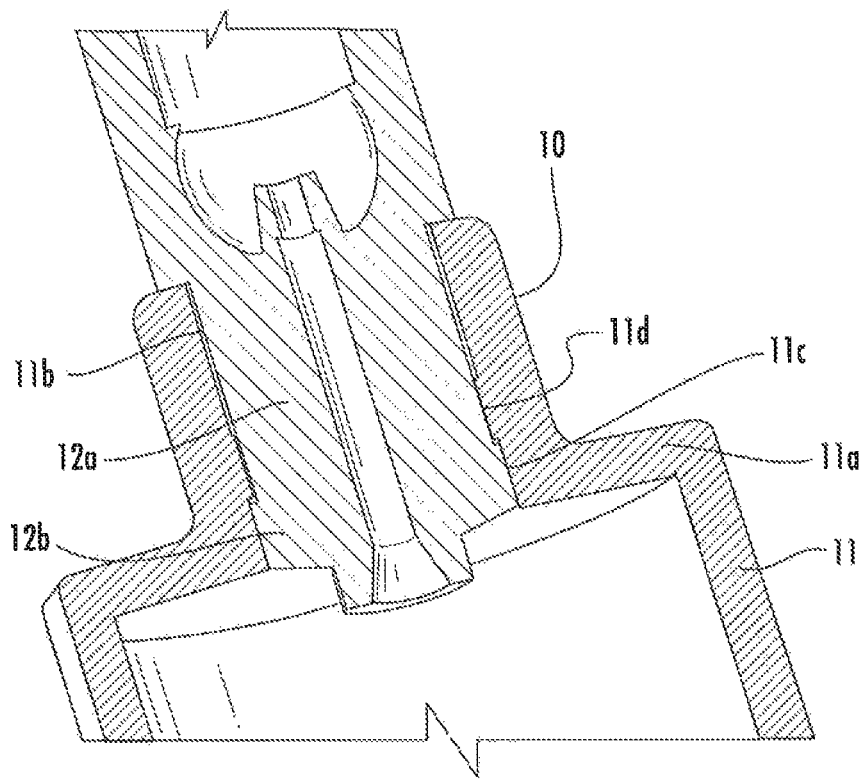
FIG. 5 is a graphic to a larger scale of the connection, when connected.
Figure 6:
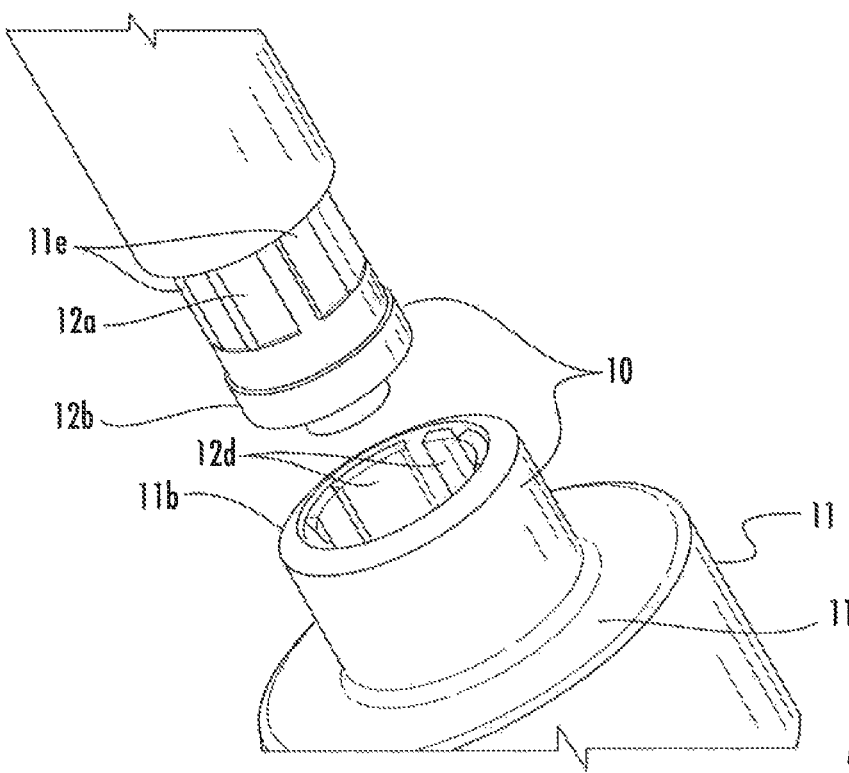
FIG. 6 is a graphic like FIG. 5 of the connection, separated.
Figure 10:
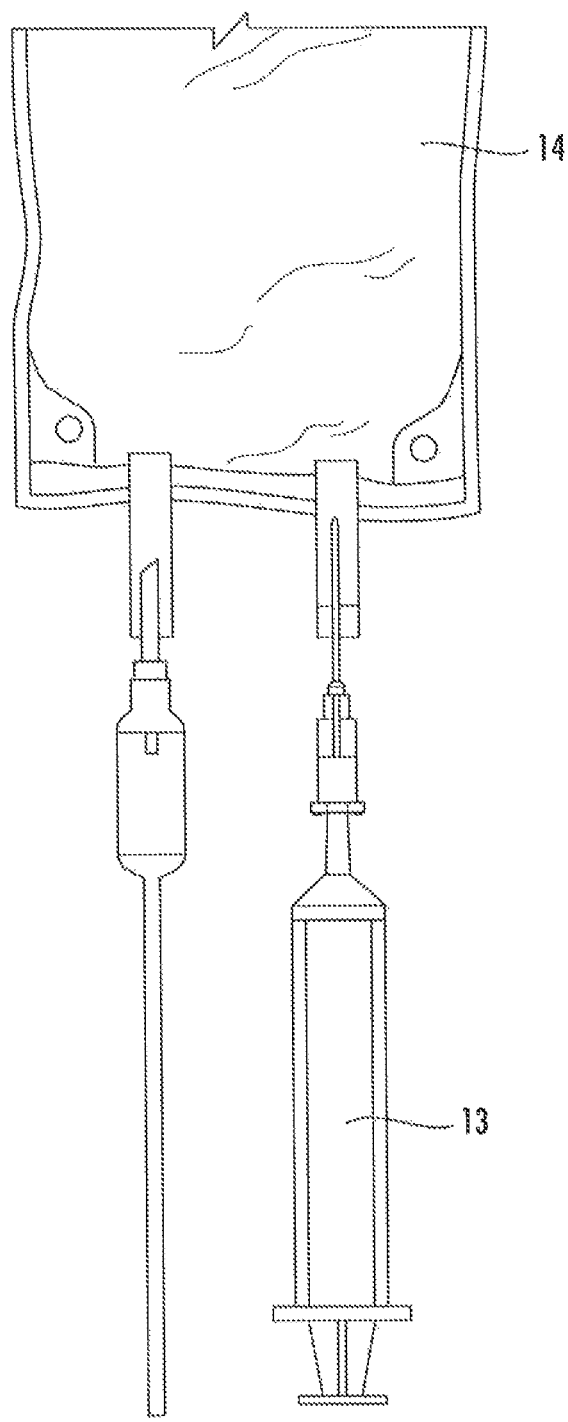
FIG. 10 is a depiction of an IV bag with a syringe in place to deliver medication.

The drawings illustrate comprises a connection 10 between a guard tube 11 and a needle holder 12 for a syringe 13 shown vestigially in FIG. 7 and in FIG. 10, for injecting medication into an IV bag 14, FIG. 10. The guard tube 11 has a needle holder receiving end 11a having an aperture 11b for the needle holder 12 to be inserted from the outside, the aperture 11b terminating at an inner end face 11c.

The needle holder 12 has an aperture-penetrating portion 12a having a rim 12b wider than a step 11d in the aperture 11b that can be pushed through the aperture 11b to snap fit over the step 11d and resist retraction therefrom by a force retraction therefrom by a force F which is greater than forces normally experienced by the aperture penetrating portion after it has effected a snap fit A value for the force F of 30 N has been found adequate to prevent accidental retraction, though a value of 40 N is preferred.

The required resistance is achieved by a combination of materials and Dimensions.

The entrance to the step 11d in the aperture 11b and the rim 12b are rounded or chamfered so that pushing the rim 12b into the aperture either spreads the aperture or compresses the penetrating portion or both using a force which is manageable for manual fitting, and to an extent that the penetrating portion fits inside the aperture, enabling it to pass through. Once through, the step 11d contracts or the rim 12b expends, or both, so that the rim 12b will not come out of the aperture 11b except under a force not normally encountered.

Either the aperture or the penetrating portion or both may be made of resilient plastics material such as polypropylene, ABS or PET. Using these materials, a rim 12b having a diameter of 4.75 mm on a penetrating portion having a diameter of 4.45 mm cooperating with a step 12d having a diameter of 4.5 mm in a aperture of 4.65 mm will allow insertion using forces that are manageable for manual fitting, but resist accidental separation under forces less than 30 N.

The aperture 11b and the aperture-fitting portion 12a have interengaging ribs 11e, 12d to prevent relative rotation.

The needle holder 12 is adapted to fit a syringe 13 with a luer lock fitting or a slip tip fitting, and is provided with an adapter 14 so that it will accept either syringe fitting. The adapter 14 is in the form of a flexible tab with a collar 14a that fits over the needle holder 12 and that has a luer lock fitting 14b that fits into a slip tip fitting 14c. The luer lock fitting 14b is retained in place by screwing over a thread 12e on the end of the adapter 14.

Dimensioning is important to provide a safe and effective connection. The guard tube 11 must not be so long that the needle cannot reach the IV bag seal, but must also be long enough for the needle tip to be located safely inside it, where a finger cannot reach down. When fitted, the needle tip 15 is desirably no less than 10 mm and no more than 14 mm from the open end 11e of the guard tube 11.

What is claimed:

1. A connection arrangement for connecting to an IV bag a syringe for injecting medication into the IV bag, comprising:
   a needle holder for the syringe;
   a guard tube having a needle holder receiving end and an open end, and wherein the guard tube has a length such that a needle tip is no less than 10 mm from the open end of the guard tube when the syringe is fitted in the need holder;
   the needle holder receiving end having an aperture into which the needle holder can be inserted from outside the guard tube, the aperture beginning at an aperture opening and terminating at an inner end face of the guard tube and having a step located between the aperture opening and the inner end face;
   the needle holder having an aperture-penetrating portion;
   the aperture-penetrating portion having a rim which is wider than the step;
   in which arrangement the rim can be pushed through the said aperture to snap fit over the step therein, such that the rim is retained within the aperture;
   and in which the rim resists retraction from the aperture by a force of 30N.

2. A connection according to claim 1, in which at least one of the aperture and the penetrating portion is rounded or chamfered so that pushing the penetrating portion into the aperture effects at least one of spreading the aperture and compressing the penetrating portion, to an extent that the penetrating portion fits inside the aperture, enabling it to pass through.

3. A connection according to claim 1, in which at least one of the aperture and the penetrating portion is made of resilient plastics material.

4. A connection according to claim 3, in which at least one of the aperture and the penetrating portion is made from a material selected from the group consisting of polypropylene, ABS and PET.

5. A connection according to claim 1, in which the aperture and the aperture-penetrating portion have interengaging ribs to prevent relative rotation.

6. A connection according to claim 1, in which the needle holder is adapted to fit a syringe with a fitting selected from a luer lock fitting and a slip tip fitting, and is provided with an adapter so that it will accept either syringe fitting.

7. A connection according to claim 6, in which the adapter is in the form of a flexible tab with a collar that fits over the needle holder and that has a luer lock fitting that fits into a slip tip fitting.

8. A connection according to claim 7, in which the luer lock fitting is retained in place by screwing over a thread on the end of the adapter.

9. A connection according to claim 1, wherein the needle tip is no more than 14 mm from the open end of the guard tube.

* * * * *